(12) United States Patent
Wong et al.

(10) Patent No.: US 7,087,444 B2
(45) Date of Patent: Aug. 8, 2006

(54) METHOD FOR INTEGRATION OF MICROELECTRONIC COMPONENTS WITH MICROFLUIDIC DEVICES

(75) Inventors: William S. Wong, San Carlos, CA (US); Michael L. Chabinyc, Mountain View, CA (US); Steven E. Ready, Santa Cruz, CA (US); Michael A. Kneissl, Mountain View, CA (US); Mark R. Teepe, Menlo Park, CA (US)

(73) Assignee: Palo Alto Research Center Incorporated, Palo Alto, CA (US)

( * ) Notice: Subject to any disclaimer, the term of this patent is extended or adjusted under 35 U.S.C. 154(b) by 298 days.

(21) Appl. No.: 10/320,904

(22) Filed: Dec. 16, 2002

(65) Prior Publication Data

US 2004/0115861 A1 Jun. 17, 2004

(51) Int. Cl.
*H01L 21/00* (2006.01)

(52) U.S. Cl. .............................. 438/22; 438/6; 438/7; 438/16; 438/31

(58) Field of Classification Search ............ 438/6, 438/7, 14, 16, 31, 69, 70, 82, 99, 108, 116, 438/118, 125, 149, 151, 311, 328, 403, 606, 438/778, 780, 800, 22, 24, 25, 102
See application file for complete search history.

(56) References Cited

U.S. PATENT DOCUMENTS

| | | | | |
|---|---|---|---|---|
| 5,238,877 A | * | 8/1993 | Russell | 438/31 |
| 5,658,515 A | | 8/1997 | Lee et al. | 264/219 |
| 5,779,868 A | * | 7/1998 | Parce et al. | 204/604 |
| 5,885,470 A | * | 3/1999 | Parce et al. | 216/33 |
| 5,936,730 A | | 8/1999 | Foley et al. | 356/344 |
| 5,942,443 A | * | 8/1999 | Parce et al. | 436/514 |
| 5,948,694 A | | 9/1999 | Reber et al. | 436/518 |

(Continued)

OTHER PUBLICATIONS

Harrison, et al., "Micromachining a Miniaturized Capillary Electrophoresis–Based Chemical Analysis System on a Chip", *Science,* 1993, 261, 895–897.

Effenhauser, et al., "Integrated Capillary Electrophoresis on Flexible Silicone Microdevices: Analysis of DNA Restriction Fragments and Detection of Single DNA Molecules on Microchips", *Analytical Chemistry,* 1997 69(17): 3451–3457.

Burns, et al., "An Integrated Nanoliter DNA Analysis Device", *Science,* 1998, 282, 484–487.

Duane Lindner, The μChemLab™ project: micro total analysis system R & D at Sandia National Laboratories, The Royal Society of Chemistry, Lab on a Chip, 2001, 1, p. 15N–19N.

J. R. Wendt, et al, Fabrication of high performance microlenses for an integrated capillary channel electrochromatograph with fluorescence detection, J. Vac. Sci. Technol. B 17(6), Nov./Dec. 1999 p. 3252–3255.

Michael L. Chabinyc, et al, An Integrated Fluorescence Detection System in Poly(dimethylsiloxane) for Microfluidic Applications, Analytical Chemistry, vol. 73 No. 18, Sep. 15, 2001, p. 4491–4498.

J. R. Webster, et al, Monolithic Capillary Electrophoresis Device with Integrated Fluorescence Detector, Analytical Chemistry, vol. 73, No. 7, Apr. 1, 2001, p. 1622–1626.

*Primary Examiner*—Lynne A. Gurley
*Assistant Examiner*—Stanetta Isaac
(74) *Attorney, Agent, or Firm*—Kent Chen

(57) ABSTRACT

A method of forming an integrated microelectronic device and a micro channel is provided. The method offers an inexpensive way of integrating devices that are usually incompatible during fabrication, a microchannel and a microelectronic structure such as an electro-optic light source, a detector or a MEMs device into a single integrated structure.

26 Claims, 10 Drawing Sheets

U.S. PATENT DOCUMENTS

| | | | |
|---|---|---|---|
| 6,022,760 A * | 2/2000 | Lebby et al. | 438/123 |
| 6,039,897 A * | 3/2000 | Lochhead et al. | 264/1.24 |
| 6,048,699 A | 4/2000 | Foley et al. | 435/6 |
| 6,100,541 A | 8/2000 | Nagle et al. | 250/573 |
| 6,203,757 B1 * | 3/2001 | Lu et al. | 422/58 |
| 6,232,136 B1 * | 5/2001 | Zavracky et al. | 438/30 |
| 6,251,343 B1 * | 6/2001 | Dubrow et al. | 422/102 |
| 6,303,288 B1 | 10/2001 | Furcht et al. | 435/4 |
| 6,312,968 B1 * | 11/2001 | Shimabukuro et al. | 438/30 |
| 6,316,781 B1 | 11/2001 | Nagle et al. | 250/573 |
| 6,358,387 B1 | 3/2002 | Kopf-Sill et al. | 204/603 |
| 6,386,050 B1 * | 5/2002 | Yin et al. | 73/861.95 |
| 6,399,952 B1 | 6/2002 | Maher et al. | 250/458.1 |
| 6,423,552 B1 * | 7/2002 | Lu et al. | 438/1 |
| 6,518,168 B1 * | 2/2003 | Clem et al. | 438/623 |
| 6,562,127 B1 * | 5/2003 | Kud et al. | 117/94 |
| 6,562,648 B1 * | 5/2003 | Wong et al. | 438/46 |
| 6,583,445 B1 * | 6/2003 | Reedy et al. | 257/82 |
| 6,653,136 B1 * | 11/2003 | Dodgson et al. | 435/461 |
| 2001/0053618 A1 * | 12/2001 | Kozaki et al. | 438/933 |
| 2002/0031838 A1 | 3/2002 | Meinhart et al. | 436/514 |
| 2002/0081773 A1 * | 6/2002 | Inoue et al. | 438/108 |
| 2002/0096994 A1 * | 7/2002 | Iwafuchi et al. | 313/495 |
| 2002/0176804 A1 * | 11/2002 | Strand et al. | 422/100 |
| 2003/0017579 A1 * | 1/2003 | Corn et al. | 435/287.2 |
| 2003/0027082 A1 * | 2/2003 | Wong et al. | 430/322 |
| 2003/0147333 A1 * | 8/2003 | Tokuda et al. | 369/121 |
| 2004/0021935 A1 * | 2/2004 | Kitamori et al. | 359/368 |
| 2004/0036731 A1 * | 2/2004 | Ready et al. | 347/19 |
| 2004/0101987 A1 * | 5/2004 | Chabinyc et al. | 438/30 |

* cited by examiner

Table 3

| MATERIAL | REFRACTIVE INDEX |
|---|---|
| PDMS | 1.43 |
| PMMA | 1.49 |
| PCPM | 1.63 |
| epoxy | 1.45-1.56 |
| polyimide | 1.52-1.53 |
| glass | 1.42 |
| H$_2$O | 1.33 |

FIG. 3

METHOD FOR INTEGRATION OF MICROELECTRONIC COMPONENTS WITH MICROFLUIDIC DEVICES

FIELD OF INVENTION

The invention relates to microfluidic devices. In particular the invention relates to a method for integrating microfluidic channels onto a substrate including a microelectronic structure such as a source of light or a light detector.

BACKGROUND OF THE INVENTION

Integrated microsystems have a number of important applications, especially in the field of biological material analysis. Such systems typically direct a light source at a sample and detect the light reflected from, transmitted through, or fluorescing from the sample.

One problem impeding wide adaptation of such integrated microsystems is the cost and complexity of such systems. In order to minimize cross contamination between biological samples, microchannels carrying the biological samples are typically designed to be disposable. Thus each microsystem needs to be inexpensive and simple to fabricate.

Microfluidic devices are generally made by subtractive processes, such as etching features into a glass or silicon substrate ("Micromachining a Miniaturized Capillary Electrophoresis-Based Chemical Analysis System on a Chip" Harrison, D. J.; Fluri, K.; Seiler, K.; Fan, Z.; Effenhauser, C. S.; Manz, A.; Science 1993 261 895–897), or by a molding procedure, typically using a polymeric material ("Integrated Capillary Electrophoresis on Flexible Silicone Microdevices: Analysis of DNA Restriction Fragments and Detection of Single DNA Molecules on Microchips" Effenhauser, C. S.; Bruin, G. J. M.; Paulus, A.; Ehrat, M.; Anal. Chem.; 1997; 69(17); 3451–3457). As will be explained, these processes impart limitations on the fabrication of totally integrated devices.

Both microfluidic channels and electronic elements can be fabricated using conventional processing on silicon substrates ("An Integrated Nanoliter DNA Analysis Device" M. A. Burns, B. N. Johnson, S. N. Brahmasandra, K. Handique, J. R. Webster, M. Krishnan, T. S. Sammarco, P. M. Man, D. Jones, D. Heldsinger, C. H. Mastrangelo, and D. T. Burke; Science 1998 Oct. 16; 282: 484–487). Typically, the same substrate material is used to form the passive fluidic channels and to serve as the growth substrate upon which the active electronic devices are grown. However, such techniques result in a low density of active devices being processed on each growth substrate because the passive channels typically cover a large area relative to the electronic devices. The high cost of silicon processing associated with active device formation and the low density of active devices on the growth substrate makes this process expensive. In addition, it may be difficult to add components from other solid-state materials such as III–V semiconductors.

Molding procedures are sometimes used to fabricate passive microfluidic channel structures. While molding can be done with relatively high precision, it is difficult to integrate active electronic devices with good registration between the channels and electronic devices using conventional molding processes ("An Integrated Fluorescence Detection System in Poly(dimethylsiloxane) for Microfluidic Applications" M. L. Chabinyc, D. T. Chiu, J. C. McDonald, A. D. Stroock, J. F. Christian, A. M. Karger, G. M. Whitesides, and "Fluidics Cube for Biosensor Miniaturization"; J. M. Dodson, M. J. Feldstein, D. M. Leatzow, L K. Flack, J. P. Golden, and F. S. Ligler Anal. Chem., 73 (15), 3776–3780, 2001).

Another difficulty with current fabrication techniques is that combining dissimilar elements by direct growth and micromachining on the same substrate to form a single integrated unit has proven to be technically difficult. For example, the microchannels, the semiconductor light emitters and detectors are formed from materials that are incompatible such that fabrication together in a single process results in poor quality devices. This incompatibility stems partly from the fact that thermal processing stability and thermal management techniques used in the fabrication of most high efficiency optoelectronic light sources are incompatible with the formation of plastic or glass structures that are typically used to form a microchannel.

Thus an improved method of fabricating a microsystem that integrates a micro-fluidic channel aligned with other electronic or opto-electronic component onto a single platform at a reduced cost and complexity is desired.

SUMMARY OF THE INVENTION

A method for integrating an electronic device structure and microchannel onto a substrate is described. The method includes forming a structure such that the structure is fixed to a substrate. Channel features are fabricated on the substrate aligned in close proximity to the structure. A mold is formed over the channel features. Finally the channel features are removed to create a channel that transports a fluidic sample being tested. The channel is positioned such that structure interacts with the channel.

BRIEF DESCRIPTION OF THE DRAWINGS

FIG. 3 is a table listing possible mold materials used to fabricate the channel walls and their respective indexes of refraction.

DETAILED DESCRIPTION

Figure 1:
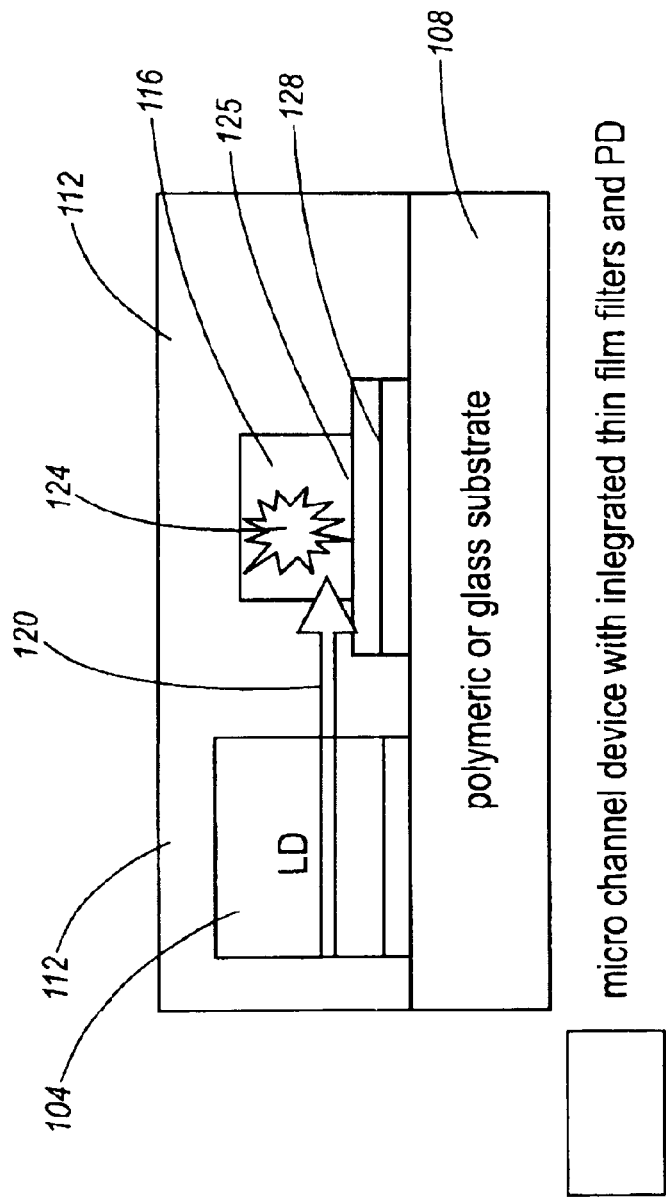
FIG. 1 shows one embodiment of a simple microchannel device with integrated thin film filters and photo detectors.

A method and structure for integrating optoelectronic components with microfluidic devices is provided. FIG. 1 illustrates a typical integrated structure that may be formed. In FIG. 1, a light source 104 such as a laser diode is bonded to a substrate 108. A housing material 112, typically epoxy or a polymer such as poly(dimethylsiloxane) PDMS, bonded to the same substrate 108 forms a microchannel 116 that carries a sample to be tested.

Light 120 emitted by light source 104 propagates through housing material 112 and is incident upon the sample 124 being tested. Sample 124 scatters incident light, both reflecting, refracting, or fluorescing light through filter 125 a detector 128, such as a silicon photodetector. Information about the sample can be obtained by measuring the frequency, intensity and other parameters of the detected light.

Figure 2:
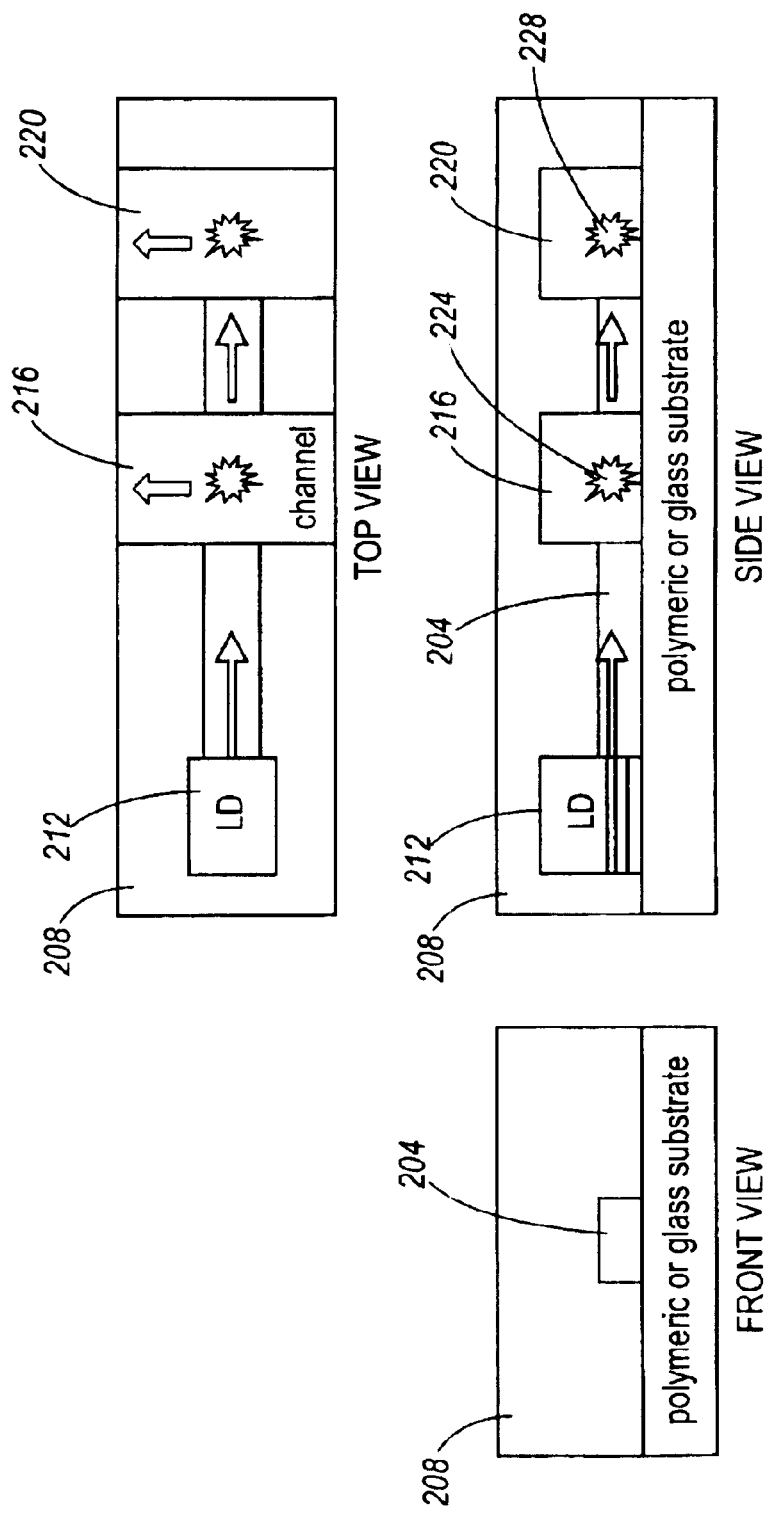
FIG. 2 shows a waveguide implemented in an integrated microstructure.

In order to further guide the light emitted by light source 104 a waveguide may be integrated into the housing material 112. The waveguide guides the light from light source 104 to the channel or a plurality of channels. FIG. 2 shows a waveguide 204 integrated into second housing material 208. FIG. 3 shows a table that lists possible materials used to fabricate second housing material 208 and waveguide 204. PDMS is a convenient housing material due to its compatibility with plastic substrates and its minimal autofluorescence characteristics. Minimal autofluorsecence is important in fluorescent detection systems. Epoxies have the advantage of being compatible with thin-film layer lift-off and transfer techniques and being relatively non-reactive to biological materials. By integrating other materials listed in table 3 with PDMS or epoxy, the index of refraction can be controlled to form waveguide 204 through the housing material. Integration of the waveguide into housing material 208 allows more efficient collection and concentration of light from light source 212. The structure shown in FIG. 2 includes two channels 216, 220 enabling the testing of two samples 224, 228.

Figure 4:
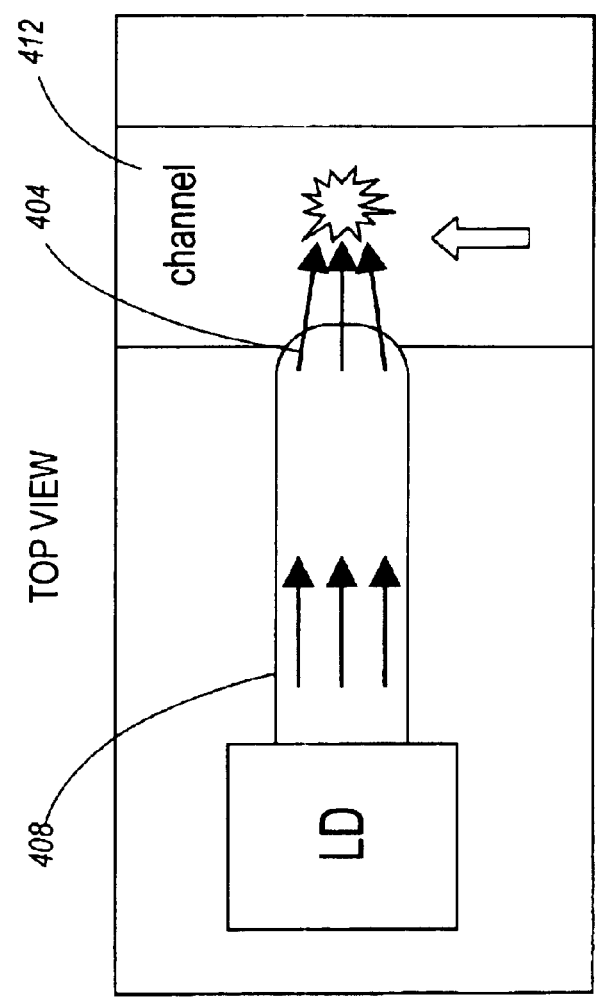
FIG. 4 shows an integrated light source and microchannel including a lens integrated into a microchannel wall.

The technology that enables integrating waveguides into the housing also allows lenses to be formed to concentrate light from the light source. FIG. 4 shows a lens 404 coupled to the termination of waveguide 408. Lens 404 focuses light into channel 412. Using a lens 404 to focus light into a smaller spot size substantially improves the spatial resolution of a biodetection chip formed from the structure of FIG. 4.

Figure 5:
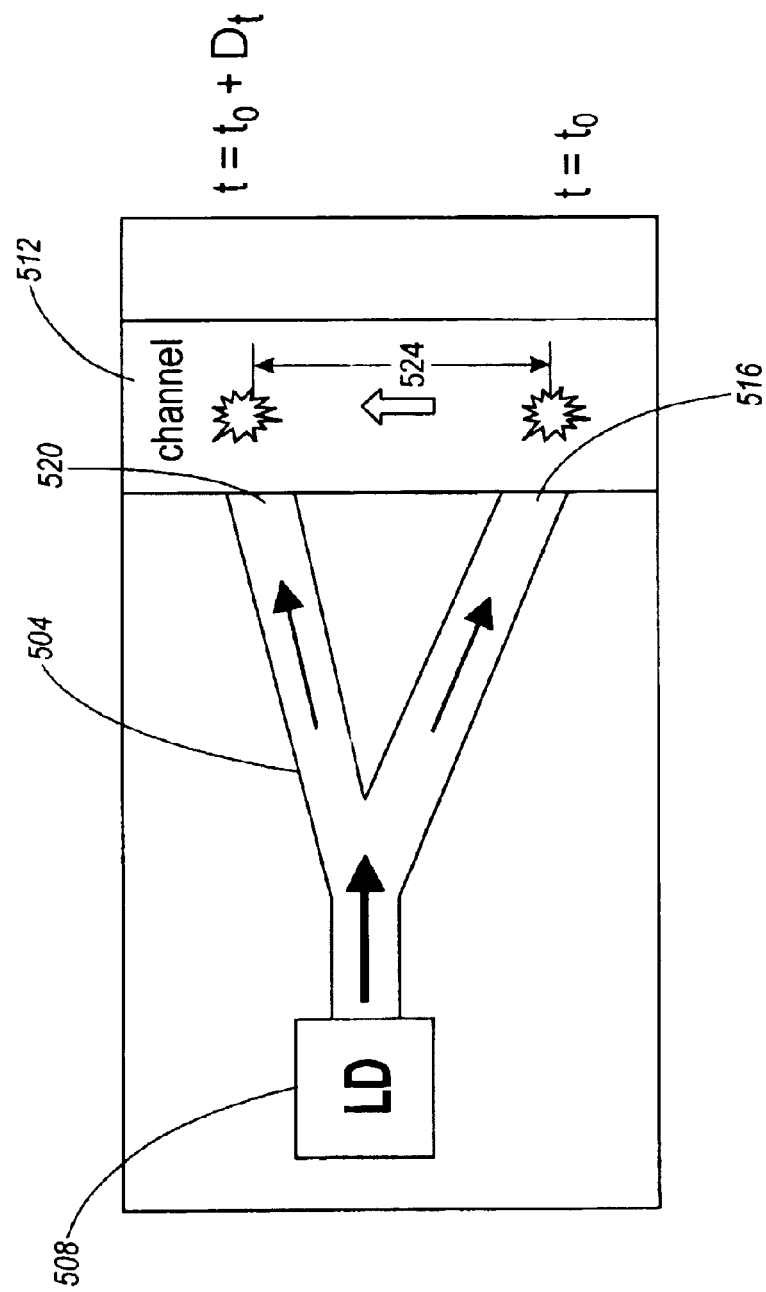
FIG. 5 shows an integrated light source and microchannel including a waveguide that divides light from the light source.

Alternately, a waveguide can divide the output of a light source into two different light paths. FIG. 5 shows a waveguide 504 that divides light from a light source 508 into two components enabling monitoring of a sample flowing along channel 512. By measuring the time delay between closely spaced events, the flow speed, and/or spatial distribution of the biomolecules in solution can be detected. For example, when an opaque object reaches a first beam 516, the object causes a drop in reflected light intensity at a first time, $t_0$. When the same object reaches a second beam 520, the object causes a second drop in reflected light intensity at time $t_0$+(change in time). The flow speed is then determined by dividing the distance 524 between first beam 516 and second beam 520 by the (change in time).

FIGS. 6–14 describe several methods of fabricating the structures shown in FIGS. 1–5. FIGS. 6–14 show a process flow that describes fabrication of an integrated optoelectronic system including a microfluidic channel. Although FIGS. 2, 4 and 5 show various embodiments of a microfluidic channel structure using waveguides and optics, the procedures shown in FIGS. 6–14 will describe general fabrication of a light source and a microchannel. The procedure may be easily modified to add waveguides and lenses by adjusting the index of refraction of the molding material during fabrication. In alternate embodiments, the light source is positioned close enough to the microchannel and the sample being tested that waveguides and lenses to direct the light are unnecessary.

Figure 6:
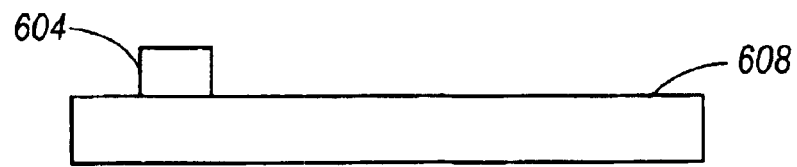
FIGS. 6–9 shows the process of forming a light source and integrating it onto a substrate.

FIG. 6 illustrates a light emitting device or light source 604 such as a GaN based laser diode or other edge-emitting laser fabricated on a growth substrate 608. The growth substrate is material is typically selected to lattice match to the laser diode. Sapphire is one example of a material that provides a good lattice match to a GaN based laser diode.

Figure 7:
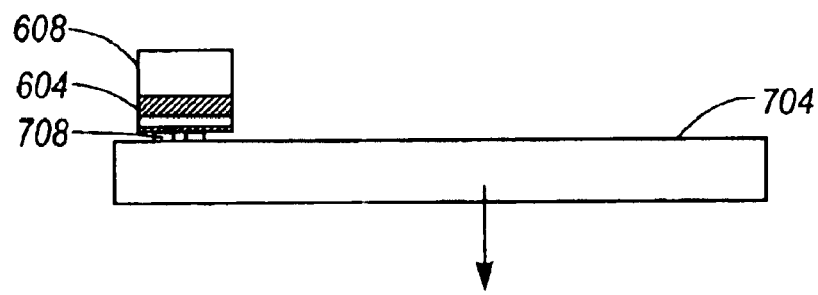

In FIG. 7, the light source 604 is flip-chip bonded to an integrated device substrate 704. The gap between light source 604 and device substrate 704 may be filled with a bonding material 708 such as epoxy. Bonding material 708 fills the gap and creates a robust bond between device substrate 704 and light source 604.

The illustrated embodiment describes flip-chip bonding, although such a design is not required. In alternate embodiments, the growth substrate serves also serves as the integrated device substrate. Thus the micro-fluidic channels are fabricated directly on the growth substrate eliminating the need for flip chip bonding. However, such a structure would be more expensive. The expense of the optical source fabrication procedure in addition to the high cost of most growth substrates, such as sapphire, makes such designs less appealing. Thus a flip chip design that allows a high density of optical devices to be formed on each growth substrate and flip chip bonds each individual optical source device to a relatively inexpensive device substrate 704 is less costly.

Figure 8:
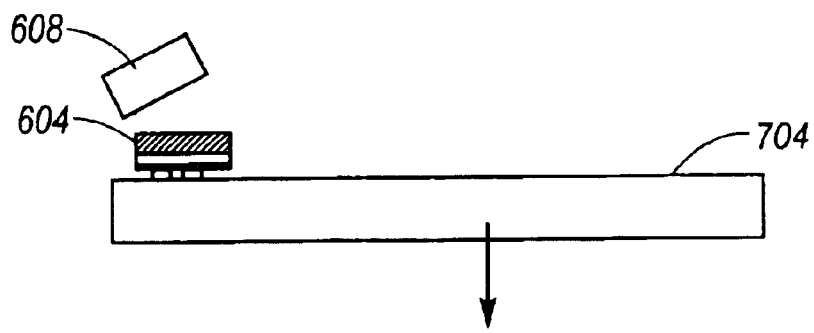

In FIG. 8, the growth substrate 608 is removed. One common method of removing growth substrate 608 uses a laser lift off process as described in U.S. patent application Ser. No. 09/648,187 entitled "Structure and Method for Separation and Transfer of Semiconductor Thin Films Onto Dissimilar Substrate Materials" filed Aug. 23, 2000 and hereby incorporated by reference. Although removal of growth substrate 608 is not required, when high heat producing light sources are used, removal of growth substrate 608 combined with the use of the flipchip mounting provides an exposed light source surface which is convenient for mounting a heat sink.

Figure 9:
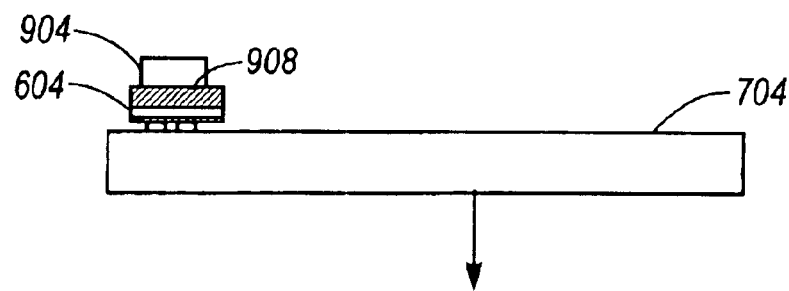

In FIG. 9, a heat sink 904 is bonded to the light source 604. When light source 604 is a semiconductor laser, especially a continuous-wave operation laser that utilizes relatively high current densities or a GaN-based blue laser, substantial heat is generated during operation. Heating of the microsystem is undesirable considering the close proximity of laser to the microchannel. Given the close proximity, excessive heating can distort the microchannel and/or substrate structure thereby degrading alignment of the light source with the microfluidic channel and detector. Excessive heat could also damage sensitive biological samples flowing through the microchannel. To avoid such damage, heat sink 904 dissipates thermal energy generated by light source 604.

One method of attaching a heat sink involves depositing a high thermal conductivity metal 908 onto the backside of exposed light source 604. The deposition may be accomplished using a variety of techniques such as spin coating, sputtering or other deposition techniques that are well known in the art. Heat sink 904 is subsequently attached or bonded to the high thermal conductivity metal.

Figure 10:
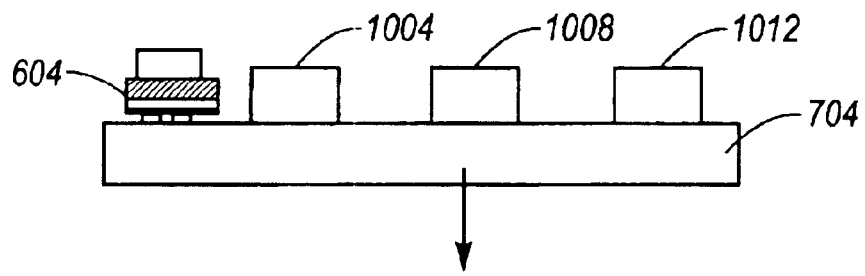
FIGS. 10–11 shows the process of forming a channel through a mold

In FIG. 10, a series of channel features 1004, 1008, 1012 are printed onto device substrate 704. Each channel feature will define a microchannel for carrying a sample material being tested. One method of forming the channel features is to use wax ink jet printing as described in U.S. patent application Ser. No. 09/838,684 entitled "Method for Printing Etch Masks Using Phase-Change Materials" filed Apr. 19, 2001 and which is hereby incorporated by reference. The channel features are usually aligned to transfer the light from the light source 604.

The alignment of features to the light source 604 or other optoelectronic device may be done using a variety of techniques. One method of achieving such alignment utilizes a sensor, such as a camera, and a feedback control system. The sensor or camera determines the position of light source 604 with respect to where a deposition mechanism, such as a piezo-electric printhead to deposit features 1004, is positioned. The feedback control system receives information from the sensor and repositions the deposition mechanism until an ideal position is achieved. The ideal position is defined to be when the deposition mechanism is positioned to form features that are aligned to light source 604. Additional details of such a control system are described in U.S. patent application Ser. No. 10/224,701 entitled "Method For The Printing Of Homogeneous Electronic Material With A Multi-Ejector Print Head" which is hereby incorporated by reference.

The proximity of each channel feature 1004 to adjacent channel features 1008, and the dimensions of the channel features are determined by the resolution of the printing system. Using special printing systems, especially printing systems that use piezo-electric drivers to generate ejection of micro-droplets as described in U.S. patent application Ser. No. 10/224701 entitled "Method for the Printing of Homogeneous Electronic Material With a Multi-Ejector Print Head" filed Aug. 20, 2002, and hereby incorporated by reference and adjusting the temperature of the ejected droplet and the device substrate surface to control spreading of the droplet as described in the previously cited reference U.S. application Ser. No. 09/838,684 entitled "Method for Printing Etch Masks Using Phase-Change Materials", very small channel features may be fabricated. Using such special print systems, the typical spacing between adjacent channels features typically ranges between 100 and 300 micrometers with each channel feature having a cross sectional width of less than 100 micrometers.

Figure 11:
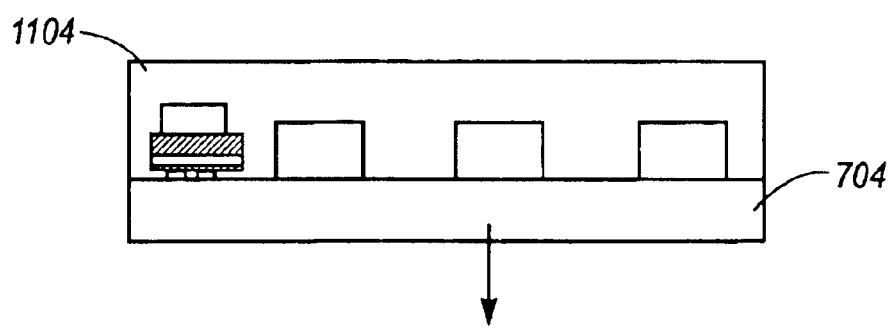

In order to fabricate micro-channels, material that forms the walls of the microfluidic channel are deposited over channel features 1004, 1008, 1012. In FIG. 11, a deposited prepolymer mold 1104 material encapsulates channel features 1004, 1008, 1012. The prepolymer mold also may or may not enclose light source 604. However, enclosing light source 604 avoids transmitting light source output through a prepolymer mold-air interface thereby avoiding light losses associated through such a transmission. In an alternate embodiment, materials with different indexes of refraction may be deposited in layers to form a waveguide in prepolymer mold 1104. Such waveguide structures were illustrated in FIGS. 2, 4 and 5.

After forming the mold, channel features 1004, 1008, 1012 are removed to create a channel for carrying a fluid sample. Four techniques will be described to remove the wax or create the channel structure, although other techniques may be used.

A first method of creating the channel structure involves waiting until prepolymer mold 1104 is cured and then dipping the channel features and mold 1104 in a solvent. The solvent dissolves the channel features leaving an open channel to transport a fluidic sample. When the channel features are a printed wax, such as Kemamide-based wax sold by Crompton Corporation of Taft, La., a suitable solvent is tetrahydrofuran or other organic solvent.

Figure 12:
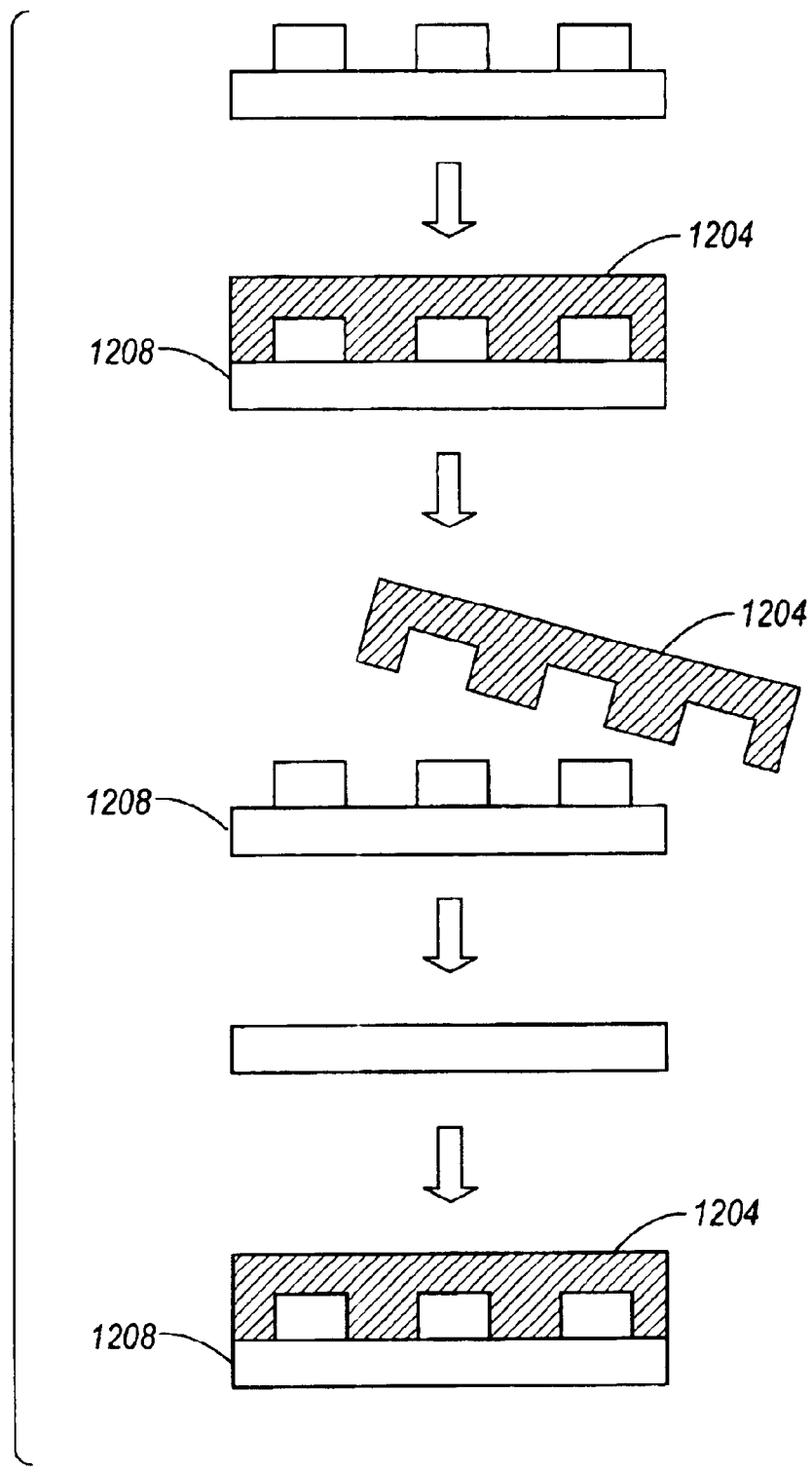
FIG. 12 shows an alternative process of forming a channel through a mold.

A second method of creating the channel structure forms prepolymer mold 1104 from a pol(dimethylsiloxane) (PDMS) material or similar material. As illustrated in FIG. 12, the PDMS mold 1204 can be cured and than peeled away from the device substrate 1208. The material used to form mold 1204 should therefore be capable of being separated from the device substrate while retaining structural integrity. After removal of PDMS mold 1204, a solvent or other stripping technique such as planarization, is used to remove channel features 1004, 1008, 1012.

After the channel features are removed, the PDMS channel mold 1204 is returned to the original position in which it was formed and reattached to device substrate 1208. The original position properly aligns the channels to the light source. The described method of removing and reattaching the mold reduces the time in which the circuit is immersed in a solvent compared to immersing the channel features in a solvent without first removing the mold. It also enables the use of other channel feature removal techniques such as planarization. However, the process of removing and reattaching the mold introduces the additional steps of realigning the PDMS channel mold 1204 with the light source and reattaching the mold A third method of forming the channels is through a backside exposure similar to that described in U.S. patent application Ser. No. 10/303,551 entitled "Method of Fabrication of Electronic Devices Using Microfluidic Channels" filed Nov. 22, 2002 and hereby incorporated by reference. This third method utilizes a transparent device substrate 704. A thin opaque film is deposited over device substrate 704. The opaque film is an etch mask used to define a pattern of micro-channels. A photosensitive polymer such as SU-8 is deposited over the patterned opaque film. Radiation transmitted through transparent device substrate 704 cures exposed regions of the photosensitive polymer in a backside exposure process. Uncured regions of the photosensitive polymer are removed, typically using a solvent such as toluene, leaving a pattern of micro channels through the cured photosensitive polymer. A cap structure formed from PDMS is placed over the channels to form capped micro-channels through which flows fluidic samples to undergo testing.

Figure 13:
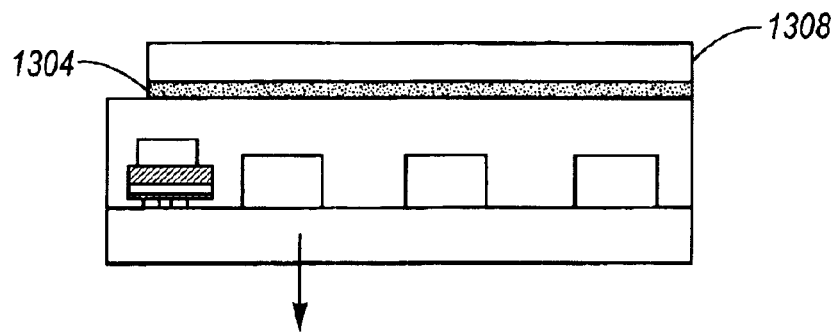
FIGS. 13–15 show the process of attaching a filter and detector to the integrated light source and microchannel structure.
Figure 14:
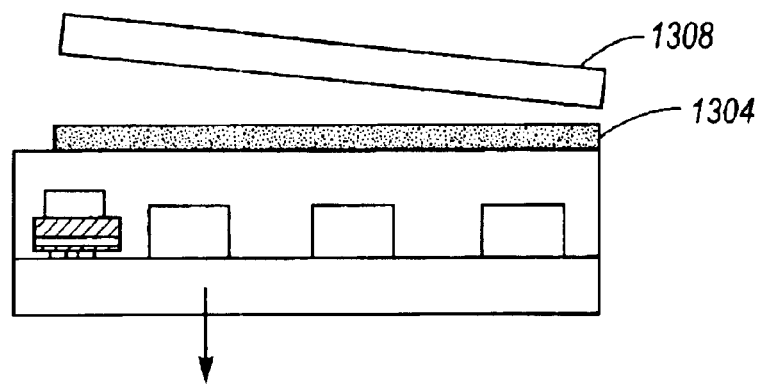
Figure 15:
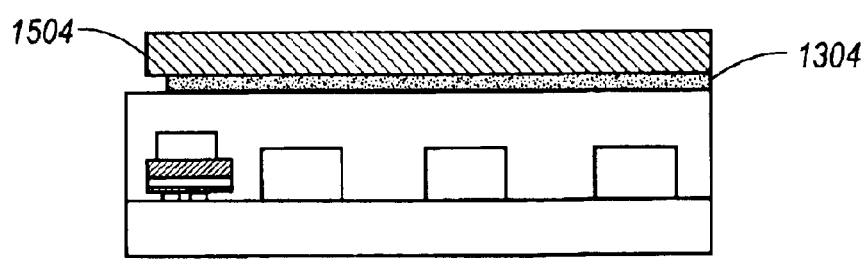

After formation of the micro-channels using any of the above described techniques, or other techniques available to those of ordinary skill in the art, a system to detect the interaction of incident light on samples flowing in the channel may be implemented. One such method is to integrate a light filter and detector above where the micro-channels have been formed. FIGS. 13–15 show one method of forming such a light filter and detector structure.

In FIG. 13, a filter 1304 is grown on a filter growth substrate 1308. Filter 1304 is bonded or otherwise attached to mold 1104. An epoxy or another adhesive may be used to bond filter 1304 to mold 1104. An appropriate filter for detecting light scattered by samples in the channel should be tuned to the frequency output of the light source. When light source 604 is an InGaN based laser that was formed on a sapphire growth substrate, an appropriate filter is a thin film of InGaN also grown on a sapphire growth substrate. The InGaN thin film layer is tuned to the output frequency of the InGaN based laser diode.

In FIG. 14, the growth substrate 1308 is removed. Removal of growth substrate 1308 may be done using a variety of techniques, including, but not limited to, laser lift-off as described in the previously cited reference U.S. patent application Ser. No. 09/648,187 entitled "Structure and Method for Speararion and Transfer of Semiconductor Thin Films Onto Dissimilar Substrate Materials", planarization of the surface or various etching techniques. After removal, of growth substrate 1308, a detector may be attached to filter 1304. FIG. 15 shows a detector 1504 attached onto filter 1304. The detector is typically a semiconductor photodetector that is sensitive to the frequency of light scattered by reflected or refracted light from the sample. Filter 1304 prevents "noise" from other light sources from reaching detector 1504.

Although the illustrated structure is suitable for many applications, one particular use for the integrated optoelectronic micro-fluidic channel structure is to perform bio-analytic testing. GaN based light emitting diodes typically emit at a wavelength between 390–530 nm which is compatible with most fluorescent dyes used in biological analysis. When collimated light sources are needed, laser diodes may be substituted for the light emitting diodes. Waveguides and lenses may be used to further focus and detect the light.

Shorter wavelength GaN based LEDs and laser diode devices targeting wavelength ranges between 260 nm and 350 nm are under development. When such devices become available, they may be combined with the integration techniques described herein to enable direct fluorescence excitation of DNA or proteins.

Longer wavelength light sources are also applicable to bio-analytical systems. The light-source used in conjunction with specific dyes sensitive to wavelengths in the red infrared regime can also be used for dye fluorescence excitation. Solid-state optoelectronic devices such as laser diodes and light emitting diodes based on the arsenide and phosphide materials system are readily available to provide the incident excitation source for the integrated bio-analytical system.

Figure 16:
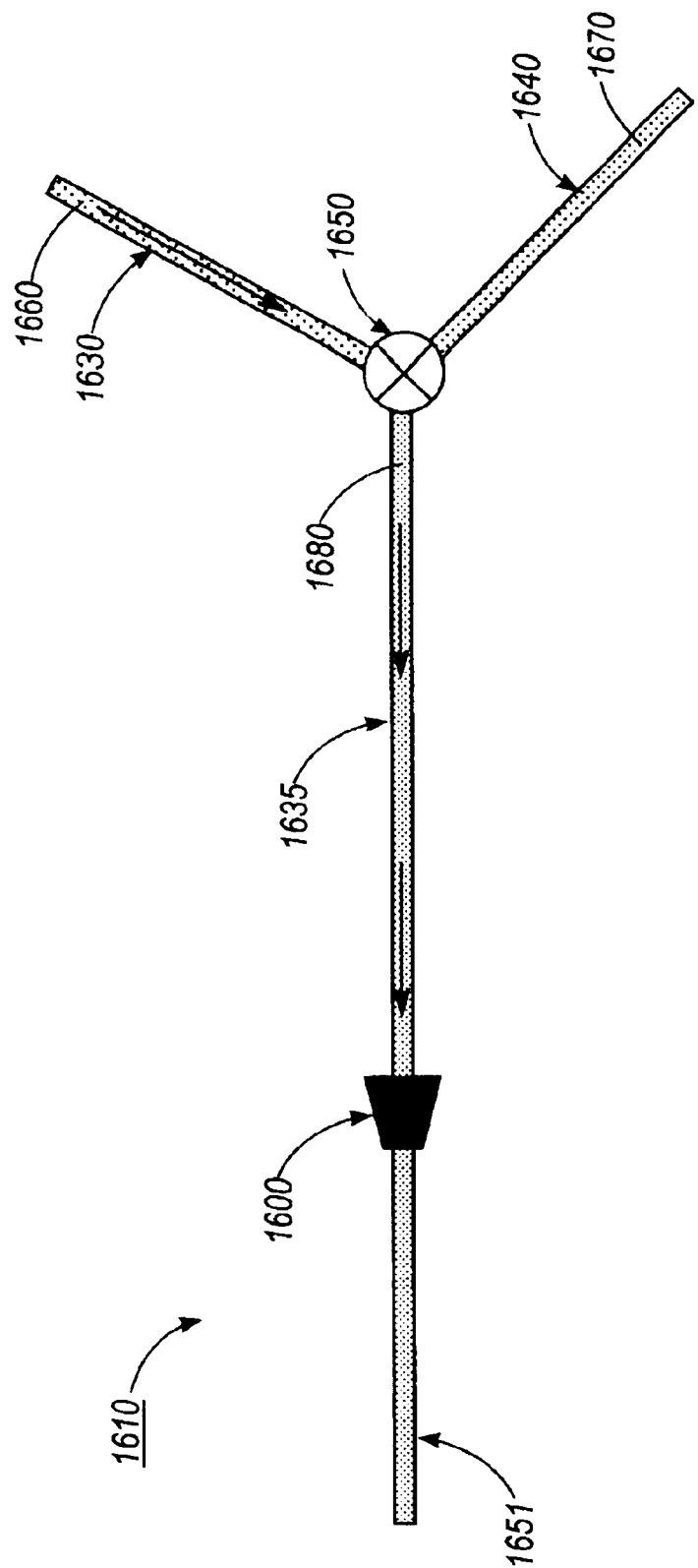
FIG. 16 shows an example MEMs structure suitable for integration with a plurality of microfluidic channels.

The interaction between electronic device structure and the fluid in the microchannel is not limited to optical excitation from a light source. The device aligned to the microchannel may also be a microelectromechanical system (MEMS) device used to pump, divert, or mix fluids within the microchannel. In one embodiment of the invention, a microchannel is aligned and positioned to a MEMS device to direct the fluid into the MEMS structure. For example, FIG. 16 shows one example of a MEMs structure or integrated device 1610 designed to pump and mix two fluids. In FIG. 16, a diverter 1650 combines two fluids, a first fluid 1660 in one channel 1630 and a second fluid 1670 from second channel 1640. The combined fluids 1680 flows into a third microchannel 1635 for delivery to separate area 1651 through micropump 1600.

The preceding description and illustrations provide many details and instructions on building and using an integrated optoelectronic device. These details are provided to facilitate understanding of the device and should not be interpreted to limit the scope of the invention. For example, many of the procedures describe using the integrated structure to test for a sample, usually a biological sample flowing in a microchannel. However, the integrated structure described has many other applications such as testing for explosives or to analyze inorganic samples. The preceding specification also provides detailed instructions on how to fabricate the integrated structure. For example, printing technology and materials used have been described. However, these techniques and materials as well as other process details may be altered and still fall within the scope of the invention. Thus, the invention should not be limited by the preceding specification but only by the claims which follow.

What is claimed is:

1. A method for integrating an electronic device structure and microchannel onto a substrate comprising:

forming the electronic device structure such that the electronic device structure is fixed to a substrate;

fabricating channel features aligned to the electronic device structure on the substrate;

forming a mold over said channel features; and, removing the channel features such that a channel to transport a fluidic sample is formed through the mold and positioned such that the electronic device structure interacts with said channel.

2. The method of claim 1 further comprising:

forming a detector on the substrate prior to the operation of forming a mold over said channel features, the detector to detect light scattered by, or fluorescing from, a fluidic sample in said channel.

3. The method of claim 1 wherein the electronic device structure is a semiconductor laser.

4. The method of claim 1 wherein the electronic device structure is a light emitting diode.

5. The method of claim 1 wherein the channel features are a phase-change material.

6. The method of claim 5 wherein the phase-change material is dissolved to create the channel structure.

7. The method of claim 5 wherein the phase-change material is deposited using a printing process.

8. The method of claim 7 wherein the printing is done by ejecting individual droplets from a printhead.

9. The method of claim 1 wherein the removal of the channel feature further comprises the operation of:

peeling off the mold from an original position over the channel features;

removing the channel features; and returning the mold to the original position.

10. The method of claim 1 wherein the mold is formed from PDMS.

11. The method of claim 10 wherein the channel features are formed from a phase-change material.

12. The method of claim 1 wherein the operation of forming the electronic device structure such that the electronic device structure is bonded to the substrate further comprises the operation of:

forming the electronic device structure on a growth substrate; and, flip-chip bonding the electronic device structure to the substrate.

13. The method of claim 12 wherein the growth substrate is sapphire.

14. The method of claim 1 wherein the channel features are uncured portions of a photosensitive polymer.

15. The method of claim 1 wherein the substrate is transparent, the operation further comprising the operation of:

forming an opaque mask, aligned to the structure, over the substrate;

depositing a photocurable polymer over the opaque mask;

transmitting radiation through the substrate to cure unmasked portions of the photocurable polymer leaving the uncured regions as features; and, removing the uncured regions.

16. The method of claim 1 wherein the electronic device structure optically interacts with the channel by transmitting a light beam into the channel.

17. The method of claim 1 wherein the electronic device structure optically interacts with the channel by receiving light from the channel.

18. The method of claim 1 wherein the electronic device structure mechanically interacts with the channel by mechanically adjusting fluid flow within the channel.

19. The method of claim 1 wherein the channel is a trench including a bottom surface and two side surfaces.

20. The method of claim 19 wherein the channel further comprises a top surface.

21. The method of claim 20 wherein a cross section of the channel is approximately rectangular in shape.

22. A method for integrating a light source and microchannel onto a transparent substrate comprising:

forming the light source such that the light source is bonded to the transparent substrate;

depositing an opaque pattern defining microchannels, aligned to the electronic device structure, over the transparent substrate;

depositing a photosensitive polymer over the opaque pattern;

transmitting radiation through the transparent substrate to cure regions of the photosensitive polymer which are not masked by the opaque pattern; and, removing the uncured regions of the photosensitive polymer to form a channel that transports a fluidic sample through the photosensitive polymer, the channel positioned such that light emitted by the source of light is directed into said channel.

23. The method of claim 22 further comprising:

forming a detector on the transparent substrate, the detector to detect light scattered by a fluidic sample in said channel.

24. The method of claim 22 wherein the light source is a semiconductor laser.

25. The method of claim 22 wherein the light source is a light emitting diode.

26. A method for integrating a light source and microchannel onto a substrate comprising:

forming the light source such that the light source is bonded to a substrate;

fabricating channel features on the substrate;

forming a mold over said channel features;

removing the mold from the substrate;

removing the channel features; and, reattaching the mold to the substrate such that a channel to transport a fluidic sample is formed through the mold and positioned such that light emitted by the source of light is directed into said channel.

* * * * *